US00PP36249P3

(12) United States Plant Patent
Matthews et al.

(10) Patent No.: US PP36,249 P3
(45) Date of Patent: Nov. 12, 2024

(54) HOP PLANT NAMED 'HS15619'

(50) Latin Name: ***Humulus lupulus* L.**
Varietal Denomination: HS15619

(71) Applicant: S.S. Steiner, Inc., Yakima, WA (US)

(72) Inventors: Paul Matthews, Yakima, WA (US); Nicholi Pitra, Yakima, WA (US); Ryan Gregory, Yakima, WA (US)

(73) Assignee: S.S. STEINER, INC., Yakima, WA (US)

( * ) Notice: Subject to any disclaimer, the term of this patent is extended or adjusted under 35 U.S.C. 154(b) by 171 days.

(21) Appl. No.: 17/975,467

(22) Filed: Oct. 27, 2022

(65) Prior Publication Data

US 2024/0147880 P1 May 2, 2024

(51) Int. Cl.
*A01H 5/02* (2018.01)
*A01H 6/28* (2018.01)

(52) U.S. Cl.
USPC ..... Plt./236

(58) Field of Classification Search
USPC ..... Plt./226, 236
See application file for complete search history.

(56) References Cited

U.S. PATENT DOCUMENTS

PP20,200 P3 8/2009 Jeske et al.

*Primary Examiner* — Karen M Redden
(74) *Attorney, Agent, or Firm* — MORRISON & FOERSTER LLP

(57) ABSTRACT

A new and distinct variety of hop plant named 'HS15619', particularly selected for its high alpha acid content, resistance to all known strains of powdery mildew currently in the Washington Yakima Valley, resistance to downy mildew, early-mid harvest maturity and exceptional cone production yields, is disclosed.

2 Drawing Sheets

Latin name:
Botanical classification: *Humulus lupulus* L.
Varietal denomination: The varietal denomination of the claimed variety of hop plant is 'HS15619'.

BACKGROUND OF THE INVENTION

The flowers (cones) of the female hop plant, *Humulus lupulus* L., are used in the making of beverages, especially beer, as a flavoring and processing component. Hops contribute towards the bitterness and aroma in beer as well as foam quality and flavor and taste stability. Various hop varieties have various special uses in the beer brewing industry. Specialized "aroma" hops are used to impart flavors by virtue of the distinct profiles of their essential oils and terpene alcohols, among other compounds, as well as to supply bitter flavors based on specific contents of bitter acids, namely, terpenophenolics, mostly humulones. Examples of aroma hops are the cultivars known as variety 'Williamette' (non-patented), variety 'Fuggle' (non-patented) and variety 'Cascade' (non-patented). Many aroma varieties are susceptible to fungal pathogens and otherwise exhibit less than ideal agronomic traits.

Hop plants, hops cones, male hop flowers, hop plant parts, hop tissue cultures and hop extracts also have bioactive properties; including anti-microbial, anti-cancer, anti-osteoporosis, anti-oxidative, anti-inflammatory, antibiotic, soporific, anti-androgenic, and pro-estrogenic activities, among others; which may be used in herbal remedies, in antimicrobial preparations for food, fodder, food fermentation, food process, animal husbandry; or in non-food uses, such as composting, bio-fuel processing, fermentation process, water treatment, animal bedding and phytoremediation; and uses in cosmetics, in nutraceutical and in pharmaceutical applications and in research thereof.

Agricultural end-product users, growers, handlers and processors of hops, of hop plants, of hop tissues and of hop products use hops and are affected by the agronomic, developmental, morphological, chemical and physical properties that vary among unique and distinct asexually reproduced varieties. Users of hops are also interested in new combinations or mixtures of hop cultivars that improve the quality of beverage flavor and process and storage properties. There exists a need for new varieties of hop plant that have improved physical and chemical properties and that are agronomically sound.

SUMMARY OF THE INVENTION

In order to meet these needs, the present invention is directed to an improved variety of hop plant. In particular, the invention relates to a new and distinct variety of hop plant (*Humulus lupulus* L.), which has been denominated as 'HS15619'.

Hop variety 'HS15619' was created during the course of a breeding program carried out at Prosser, WA. 'HS15619' was selected from a population of seedlings derived from a controlled cross-pollination in summer of 2014 between a female hop plant of German ancestry (female parent, non-patented) and a proprietary male hop plant (male parent, non-patented). The male parent is the progeny of a controlled cross-pollination between female hop plant "Apollo" (U.S. Plant Pat. No. 20,200) and a proprietary non-patented male hop plant.

Seedlings from the cross that created 'HS15619' were screened in a greenhouse for powdery mildew (*Podosphaera*

*macularis*) resistance. Non-infected seedlings were then grown in a single hill field breeding nursery at Mabton, WA for two years (2015-2016) to allow for agronomic and chemistry traits to be measured and/or assessed. The variety 'HS15619' was identified as having potential as a new cultivar. 'HS15619' was subsequently propagated via digging and dividing rhizomes in the Spring of 2017. The rhizomes were planted in pots and grown in a greenhouse in Prosser, WA in the spring of 2017 with subsequent softwood cuttings taken from the plants generated from rhizomes to propagate additional clones of 'HS15619'. The resulting plants were found to be true to type demonstrating that the characteristics of the new cultivar 'HS15619' are stable and transmitted without change through succeeding generations.

New hop variety 'HS15619' has undergone extensive evaluation and testing. In winter of 2016 it was decided to advance 'HS15619' due to its strong plant vigor, robust cone production, high alpha acid content and absence of powdery mildew and downy mildew disease infections. Second generation plants were propagated and grown in a greenhouse in Prosser, WA in spring of 2017. Eight hills of the propagated clones were planted in the spring of 2017 in a research trial hop field in Prosser, WA for agronomic testing. The field plants were evaluated for two years (2017-2018) for disease resistance, cone production yields, cone alpha acid content, cone oil content, and oil makeup. Following harvest, cones were stored to measure the stability of alpha acid and oil content over time. Results from the field trial indicated that 'HS15619' had high yield potential, exhibited disease resistance to powdery and downy mildew, high alpha acid content, and stable alpha acid during storage. It was decided to advance 'HS15619' to large plot testing in the fall of 2018. In the spring of 2019, 'HS15619' was asexually propagated using rhizome digging and divisions as well as periodic softwood cuttings at a greenhouse in Prosser, WA to produce a total of 5,000 third generation, cloned plants. These plants were planted in the spring of 2019 in a large plot research trial in a hop field at Sunnyside, WA. This planting was evaluated for two years (2019-2020) for disease resistance, cone production, cone alpha acid content, cone oil content, and oil makeup. In the spring of 2020, rhizomes were dug from the third generation planting at Sunnyside, WA and planted directly into the same field in Sunnyside, WA in the spring of 2020 to produce fourth generation plants and expand the large plot research trials. The fourth generation plants were grown and evaluated for three years (2020-2022). During all field evaluations from 2019-2022, 'HS15619' exhibited the same characteristics first observed in the first generation planting including resistance to powdery and downy mildew, high cone production yields, and very high alpha acid content. These results demonstrated that the characteristics of the new cultivar 'HS15619' are stable and transmitted without change through succeeding generations. 'HS15619' is maintained at three locations in the lower Yakima Valley between Sunnyside and it has undergone observations for uniformity at five locations throughout the Yakima Valley. All plants have been found to be true to type, that is, no off-types have been observed.

The 'HS15619' cultivar is characterized by the production of female hop cones with high, stable alpha acid content; early-mid harvest maturity between the $5^{th}$ and $15^{th}$ of September; and disease resistance to powdery mildew (*Podosphaera macularis*) and downy mildew (*Pseudoperonospora humuli*). The new cultivar is suitable as both a flavoring and processing component for beer brewing.

BRIEF DESCRIPTION OF THE DRAWINGS

This new hop plant is illustrated by the accompanying photographs. The colors shown are as true as can be reasonably obtained by conventional photographic procedures. Unless otherwise indicated, the photographs are of plants that are four months post mechanical pruning.

DETAILED BOTANICAL DESCRIPTION

Figure 1:
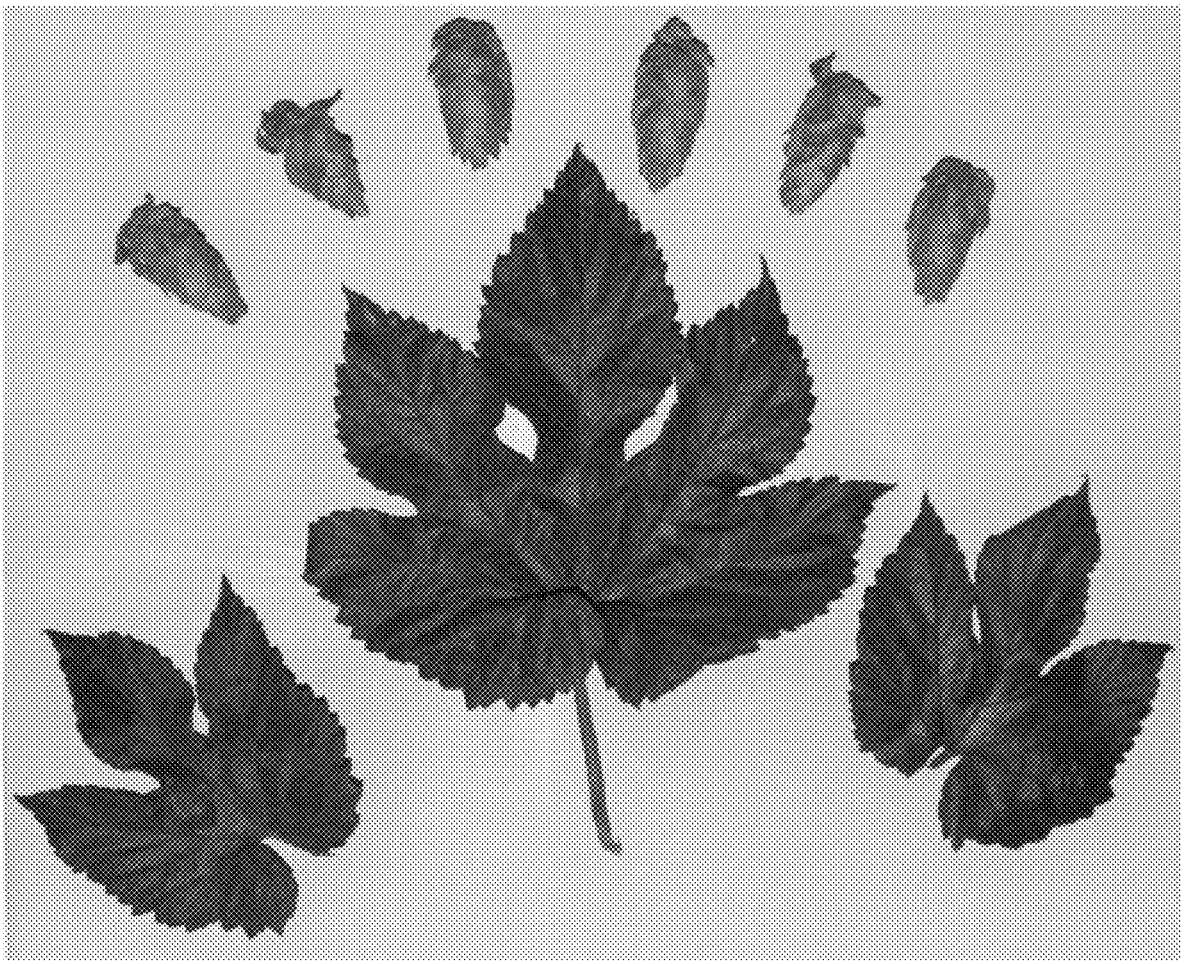
FIG. 1 illustrates cones and leaves of hop variety 'HS15619'. Photo was taken 105 days post-training of current crop year, within third crop year, 30 months post-planting.
Figure 2:
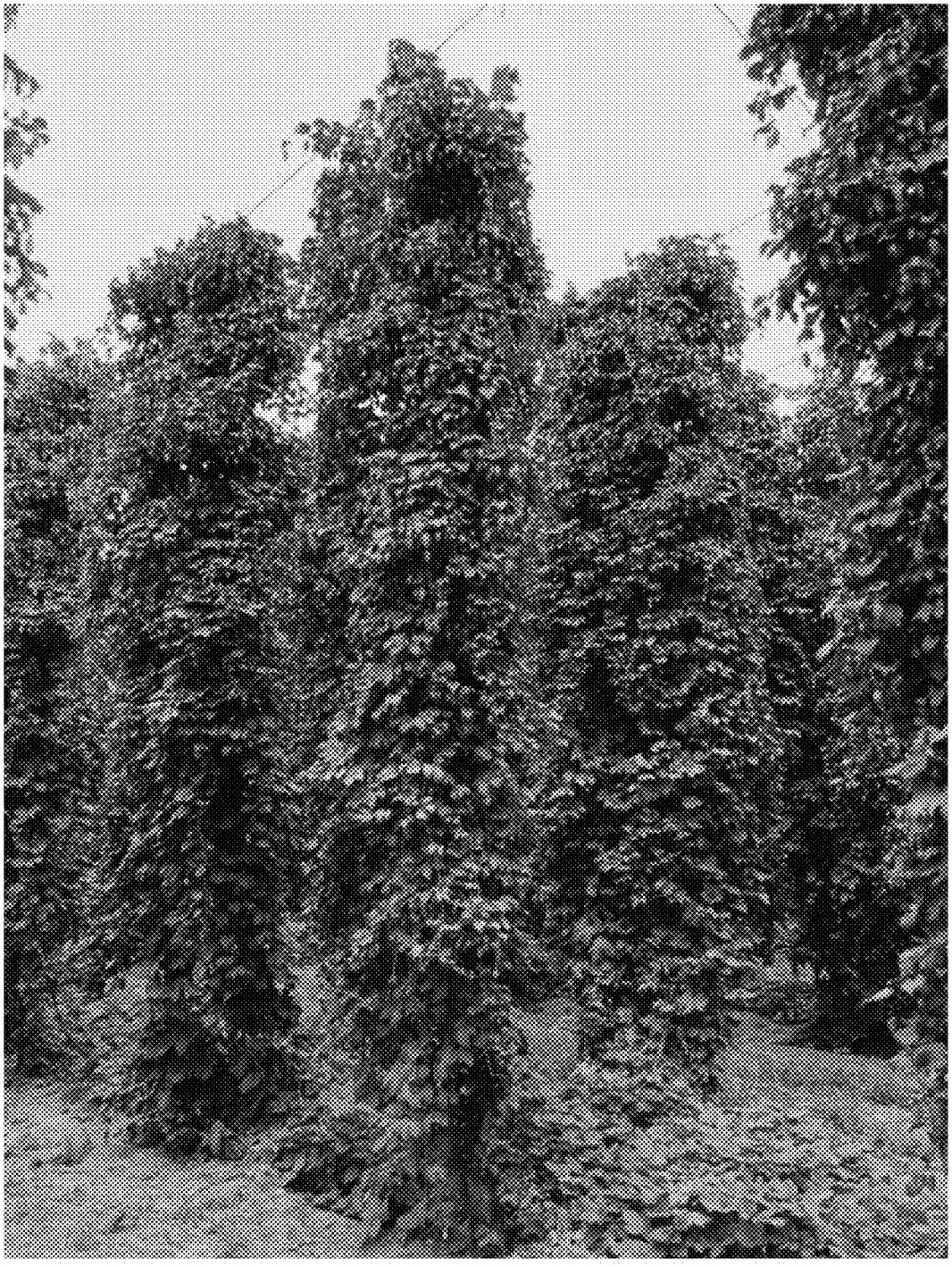
FIG. 2 illustrates whole plants of hop variety 'HS15619'. Photo was taken 105 days post-training of current crop year, within third crop year, 30 months post-planting.

The following detailed descriptions set forth the distinctive characteristics of 'HS15619'. The data which define these characteristics is based on observations taken in Sunnyside, WA from 2019-2022. This description is in accordance with UPOV terminology. Color designations, color descriptions, and other phenotypical descriptions may deviate from the stated values and descriptions depending upon variation in environmental, seasonal, climatic, and cultural conditions. 'HS15619' has not been observed under all possible environmental conditions. The botanical description of 'HS15619' was taken from plants that were four months past mechanical pruning. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* $2^{nd}$ edition by James G. Harris and Melinda Woolf Harris, unless where otherwise defined.

Classification:

*Species.*—*Humulus lupulus* L.

*Common name.*—Hop.

*Denomination.*—'HS15619'.

Parentage:

*Female parent.*—Female hop plant of German ancestry (non-patented).

*Male parent.*—Proprietary male hop plant (non-patented).

Plant:

*General.*—Made up of many parts and colors of vigorous, climbing bines.

*Growth type.*—Moderately aggressive.

*Shape.*—Columnar to obovate.

Main shoot:

*Bine color.*—Green (RHS 137C).

*Diameter (half way up vine).*—11-13 mm.

*Node pubescence.*—None, glabrous.

*Average internode length.*—217 mm.

*Anthocyanin coloration.*—Pink violet (RHS N77B).

Side shoots:

*Attitude.*—Down forked.

*From the middle third of the plant.*—Length: 155 cm. Density of foliage: Moderate. Number of cones per node: 8. Total number of cones: 96. Number of nodes per lateral: 12.

*From the upper third of the plant.*—Length: 107 cm. Number of cones per node: 6. Total number of cones: 72. Number of nodes per lateral: 12.

Stipule:

*Attitude.*—Down forked.

*Color.*—Green (RHS 137C).

Leaf:

*General.*—Palmate on main bine and cordate on side-arms.

*Length.*—12-15 mm.

*Width.*—12-15 mm.

*Length/width ratio.*—1:1.

*Predominant number of lobes.*—3.

*Blistering of upper side of blade.*—Slight blistering.

*Margin.*—Moderately serrate.

*Color of upper side of blade.*—Dark green (RHS 137A).

*Color of lower side of blade.*—Moderate yellowish green (RHS 147B).

*Intensity of green color of upper side of blade.*—Consistent intensity of dark green.

*Texture of upper side of blade.*—Glabrous.

*Texture of lower side of blade.*—Glabrous.

*Petiole.*—Length: 8 mm. Width: 5 mm. Color: Varying coloration of Green (RHS 144A) and Pink violet (RHS N77B). Texture: Rough with raised bristles.

Flowering:

*Time of flowering.*—July 5th.

*Flowering interval.*—Continuous for 20 days.

Cones:

*Length.*—45 mm.

*Width.*—20 mm.

*Length/width ratio.*—2.25:1.

*Overall shape.*—Ovate.

*Shape in cross section.*—Squircle.

*Overall color.*—Mixture of Green (RHS 137C) and Dark green (RHS 137A).

*Intensity of green color.*—Checkered pattern of green and dark green.

*Time of picking maturity of cones.*—September $5^{th}$ to $15^{th}$.

*Texture.*—Glabrous.

*Bracts.*—Color: Dark green (RHS 137A). Length: 16-20 mm. Width: 13-16 mm. Length/width ratio: 1.25. Degree of opening: Slight opening. Length of apex: 2 mm.

*Bracteoles.*—Color: Green (RHS 137C).

*Yield.*—2,800-3,400 pounds of cones per acre per season from two year old plants and above when grown in the Washington Yakima Valley.

*Analytical data of cones.*—% Alpha-acids: 18-21%. % Beta-acids: 4-5%. Alpha/beta ratio: 4.2-5.0. Cohumulone (% of alpha-acids): 26-29%. Storage characteristics: 7% transformation of alpha-acids after 6 months at 3° C. Total oils (mls/100 g): 1.0-2.0.

Resistance to abiotic stress, pests, and diseases:

*Powdery mildew (podosphaera macularis).*—Resistant.

*Downy mildew (pseudoperonospora humuli).*—Resistant.

*Winter hardiness/cold tolerance.*—Winter hardiness allows for plant perennation up to USDA Plant Hardiness Zone 5a (−20 to −15° F./−28.9 to −26.1° C.), as per the "2012 USDA Plant Hardiness Zone Map".

*Drought/heat tolerance.*—Strong heat tolerance of both first year, immature plants and mature plants up to 45° C. maximum air temperatures without negative impact on vegetive growth, reproductive maturity, or yield potential. This tolerance includes extended heat waves of multiple consecutive days with maximum air temperatures exceeding 39° C.

COMPARISONS TO PARENTAL AND REFERENCE HOP VARIETIES

'HS15619' is distinguished from its female parent as 'HS15619' has 18-21% alpha acids, 26-29% Co-Humulone, downy mildew resistance, early-mid harvest maturity and mature cone production yields of 2,800 to 3,400 pounds per acre, whereas the female parent has 10-14% alpha acids, 17-22% Co-Humulone, downy mildew tolerance, late harvest maturity and cone production yields of 1,800-2,000 pounds per acre.

'HS15619' is distinguished from its male parent as 'HS15619' produces only female flower structures that mature into cones with high alpha acid content and improved brewing qualities, whereas its male parent produces only small male flowers that produce pollen with limited brewing qualities.

Under field growing conditions in the Washington Yakima Valley, 'HS15619' is distinguished from varieties of common knowledge by the following characteristics. When compared to 'Apollo', 'HS15619' has 18-21% alpha acids, is resistant to V6 and all other known strains of powdery mildew in the Washington Yakima Valley, has early-mid harvest maturity and mature cone production yields of 2,800 to 3,400 pounds per acre, whereas 'Apollo' has 15-19% alpha acids, susceptibility to V6 powdery mildew strain, mid-late harvest maturity and cone production yields of 2,800-3,200 pounds per acre.

When compared to 'Eureka!', a non-patented female hop variety, 'HS15619' has 18-21% alpha acids, is resistant to V6 and all other known strains of powdery mildew in the Washington Yakima Valley, is resistant to downy mildew, has early-mid harvest maturity and mature cone production yields of 2,800 to 3,400 pounds per acre, whereas 'Eureka!' has 17-20% alpha acids, only tolerance to V6 powdery mildew strain, no tolerance (susceptibility) to downy mildew, late harvest maturity, and cone production yields of 2,600-3,200 pounds per acre.

When compared to 'Zeus', a non-patented female hop variety, 'HS15619' has 18-21% alpha acids, is resistant to V6 and all other known strains of powdery mildew in the Washington Yakima Valley, is resistant to downy mildew, has early-mid harvest maturity and mature cone production yields of 2,800 to 3,400 pounds per acre, whereas 'Zeus' has 12-18% alpha acids, susceptibility to V6 powdery mildew strain, susceptibility to downy mildew, late harvest maturity and cone production yields of 2,400-3,000 pounds per acre.

What is claimed is:

1. A new and distinct variety of hop plant named 'HS15619' as shown and described herein.

* * * * *